(12) United States Patent
Yeretsian

(10) Patent No.: US 8,764,778 B2
(45) Date of Patent: Jul. 1, 2014

(54) BIODEGRADABLE SUTURE CLIP FOR JOINING BODILY SOFT TISSUE

(76) Inventor: Sarkis Yeretsian, Laval (CA)

(*) Notice: Subject to any disclaimer, the term of this patent is extended or adjusted under 35 U.S.C. 154(b) by 467 days.

(21) Appl. No.: 12/832,112

(22) Filed: Jul. 8, 2010

(65) Prior Publication Data

US 2012/0010635 A1    Jan. 12, 2012

(51) Int. Cl.
*A61B 17/08* (2006.01)

(52) U.S. Cl.
USPC ............ 606/157; 606/151; 606/215; 606/216

(58) Field of Classification Search
USPC .................. 606/157, 158, 215–217, 220; 24/DIG. 38
See application file for complete search history.

(56) References Cited

U.S. PATENT DOCUMENTS

| | | | | |
|---|---|---|---|---|
| 1,452,372 A | * | 4/1923 | Gomez | 606/217 |
| 1,756,670 A | * | 4/1930 | Treat | 606/119 |
| 4,637,380 A | * | 1/1987 | Orejola | 606/216 |
| 4,924,864 A | * | 5/1990 | Danzig | 606/142 |
| 5,620,452 A | * | 4/1997 | Yoon | 606/151 |
| 6,692,507 B2 | * | 2/2004 | Pugsley et al. | 606/153 |
| 7,892,244 B2 | * | 2/2011 | Monassevitch et al. | 606/151 |
| 8,097,007 B2 | * | 1/2012 | Evans et al. | 606/151 |
| 8,128,642 B2 | * | 3/2012 | Heeps et al. | 606/142 |
| 2008/0215090 A1 | * | 9/2008 | Gonzales et al. | 606/219 |

* cited by examiner

*Primary Examiner* — Melanie Tyson
*Assistant Examiner* — Todd J Scherbel
(74) *Attorney, Agent, or Firm* — Norton Rose Fulbright Canada LLP

(57) ABSTRACT

A biodegradable suture clip for joining bodily soft tissue is described. The suture clip has a pair of identical flexible compression strips which are identical and adapted to interlock with one another. Each strip has at least two piercing teeth having pointed free ends and opposed latch formations and also has at least two tooth latching guide openings for captive engagement with the piercing teeth. The openings are provided with latching guide ramps provided with arresting gripping formations wherein opposed latch formations of the teeth engage with associated ones of the gripping formations.

5 Claims, 6 Drawing Sheets

BIODEGRADABLE SUTURE CLIP FOR JOINING BODILY SOFT TISSUE

TECHNICAL FIELD

The present invention relates to an auto-graft bio-synthetic mesh and method of use for ventral and parastomal hernias.

BACKGROUND ART

The prevalence rate of incisional hernia is 3% to 20% after 2 million laparotomies performed in the United States. Problematic factors related to development of incisional hernia include wound infection, immunosuppression, morbid obesity, previous operations, prostatism, and abdominal aneuvrysectomy.

Many ventral and parastomal hernia repair techniques have been described. Traditional primary repair involves a laparotomy with muscle or aponeurotic splitting incisions as preferred procedure to preserve the nerve and blood supply thus avoiding division of fibers, enhancing the approximation of edges of the wound when tension is increased. For these reasons transverse incisions, as shown in FIG. 1, were preferred to vertical incisions, as shown in FIG. 2. Increased intra-abdominal pressure approximate the fibers and close the defect. Closure of the wound was performed with strong non absorbable sutures. However, wide areas of soft tissue dissection increases bleeding during surgery as well as wound infection and related wound complications (12% and more).

These inherent complications have increased the interest in developing new surgical techniques for repairing the ventral and parastomal hernias without large subcutaneous raising/dissecting flaps and without bilateral fascial incisions of traditional hernia repair.

SUMMARY OF INVENTION

It is a feature of the present invention to provide an auto-graft bio-synthetic mesh for the repair of ventral and parastomal hernias and which substantially overcomes all of the above-mentioned disadvantages of the prior art.

Another feature of the present invention is to provide an auto-graft bio-synthetic mesh which is formed of woven synthetic fibers and configured as a substantially circular mesh or as a patch of the mesh having a substantially circular delineation thereon to provide guidance to a surgeon for the formation of stitches in at least two substantially concentric circles to secure the mesh to the parietal peritoneum and the posterior sheath of the rectus muscle.

Another feature of the present invention is to provide an auto-graft bio-synthetic circular mesh wherein the mesh is secured by two substantially concentric circles of stitches, a first outer peripheral circle of stitches and a second inner circle of stitches.

According to another feature of the present invention the woven fibers are one of polyester or polypropylene or biodegradable polymers which are coated with the patient's tissue or coated with patient collagen.

Another feature of the present invention is to provide a method of wound closure using an auto-graft bio-synthetic fiber mesh for the repair of ventral and parastomal hernias.

Another feature of the present invention is to provide a suture clip for joining portions of bodily soft tissue to close an incision.

According to the above features, from a broad aspect, the present invention provides an auto-graft bio-synthetic mesh for ventral and parastomal hernia repair wherein an abdominal incision is effected through the alba linea and the peritoneum for access to the intra-peritoneal cavity. The mesh is formed of woven synthetic fibers and is one of a substantially circular mesh or a mesh having a substantially circular delineation thereon whereby to provide guidance for the formation of stitches in at least two substantially concentric circles to secure the mesh to the parietal peritoneum and the posterior rectus sheath. The mesh permits the hernia repair without dissecting the subcutaneous flaps and without bilateral fascial relaxing incisions.

According to a further broad aspect of the present invention there is provided a method of wound closure wherein an abdominal incision is effected through the alba linea and the peritoneum for access to the intra-peritoneal cavity for the repair of ventral and parastomal hernias. The method comprises providing a flexible bio-synthetic mesh formed of woven synthetic fibers and wherein the mesh is one of a substantially circular mesh or a mesh having a circular delineation thereon. The mesh is introduced in the peritoneal cavity through the abdominal incision. Stitches are applied all about an outer circle of the mesh and an inner circle to secure the mesh to the parietal peritoneum and the posterior rectus sheath and wherein the mesh permits the hernia repair without dissecting the subcutaneous flaps and without bilateral fascial relaxing incisions. The abdominal incision is then closed over the mesh.

According to a further broad aspect of the present invention there is provided a suture clip for joining portions of bodily soft tissue. The suture clip comprises a pair of identical flexible compression strips adapted to interlock with one another with the portions of bodily soft tissue compressed therebetween to arrest blood vessels in the portions of bodily soft tissue. Each compression strip has at least two equidistantly spaced-part tissue piercing teeth projecting from a clamping surface of the strip. Each piercing tooth has a pointed free end portion. At least one latch formation is associated with the pointed free end portion. At least two retention means are formed integral with the strip and each disposed between two of the piercing teeth for latching engagement of at least one latch formation with the teeth of one strip aligned with the retention means of the other strip.

BRIEF DESCRIPTION OF DRAWINGS

A preferred embodiment of the present invention will now be described with reference to the accompanying drawings in which.

DESCRIPTION OF PREFERRED EMBODIMENTS

Figure 1:
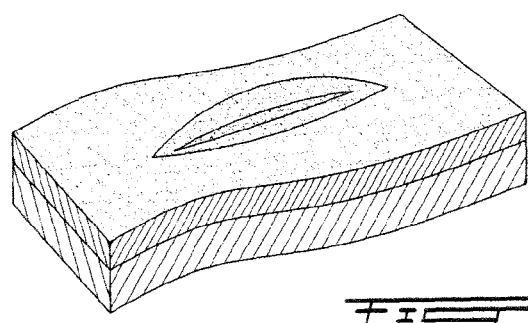
FIG. 1 is perspective view illustrating a vertical incision wherein intra-abdominal tension separates edges of the incision.
Figure 2:
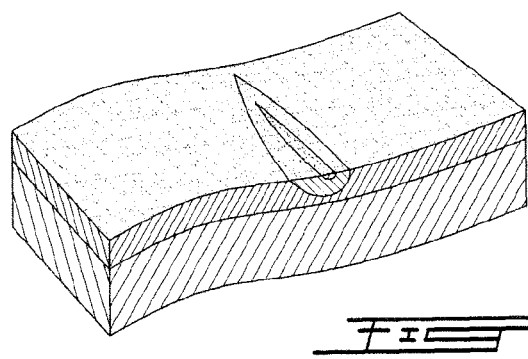
FIG. 2 is a perspective view of a transverse or horizontal incision.
Figure 3:
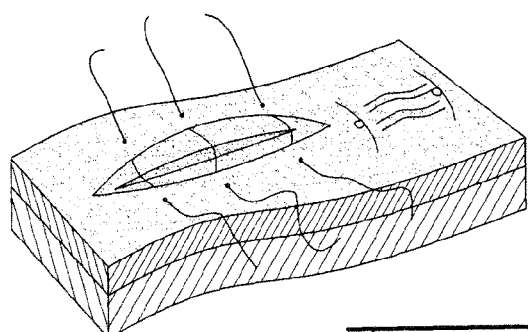
FIG. 3 is a perspective view illustrating the application of fiber stitches for the closure of the vertical incision as shown in FIG. 1.
Figure 4:
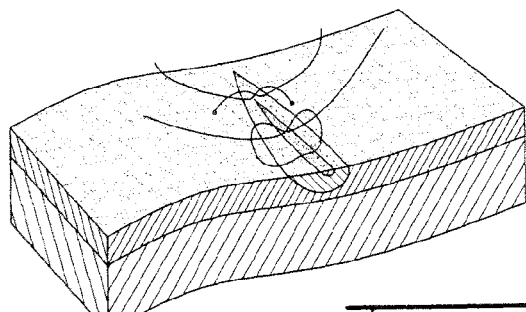
FIG. 4 is a perspective view illustrating the application of stitches for closing a transverse incision as shown in FIG. 2 and wherein shearing or splitting of the stitch fibers occurs.
Figure 8:
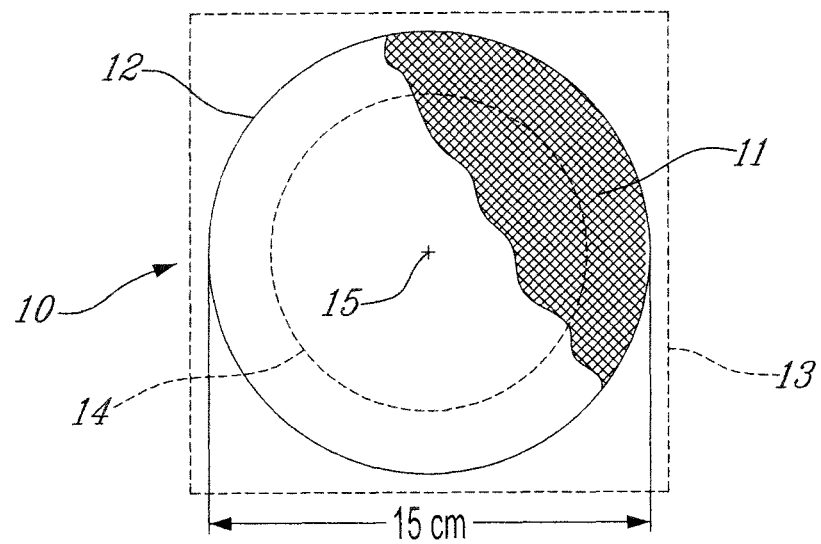
FIG. 8 is a side elevation view of the circular auto-graft bio-synthetic mesh of the present invention and illustrating modifications thereof.

Referring now to the drawings, FIGS. 1 to 4 illustrate known closure repairs of transverse and vertical abdominal incisions when repairing hernias and which exhibit complications which are obviated by the repair technique of the present invention using the auto-graft bio-synthetic mesh as illustrated in FIG. 8. FIG. 1 illustrates a transverse incision while FIG. 2 illustrates a vertical incision and wherein intra-abdominal tension separates edges of the incisions. FIG. 3 illustrates the repair of a vertical incision as shown in FIG. 1 by the application of fiber stitches and which are less susceptible to rupture as they extend transversely of the tissue fiber direction whereas as shown in FIG. 4, shearing or splitting of fibers occurs when stitching a transverse incision.

Referring to FIG. 8, there is shown generally at the auto-graft bio-synthetic mesh constructed in accordance with the present invention and which was developed for wound closure in the repair of ventral or parastomal hernias wherein an abdominal incision is effected through the alba linea and the peritoneum for access to the intra-peritoneal cavity 9 for access to the hernia. The bio-synthetic patch 10 is a flexible patch of woven synthetic fibers 11 which may be polyester or polypropylene fibers or biodegradable polymers, as will be described later. The patch may be of circular configuration wherein the outer periphery 12 is circular or it may be rectangular as illustrated by phantom line 13 or have any other outer shape provided that a substantially circular delineation can be effected thereon, such as by printing, crimping or otherwise, to delineate a circle representative of a circle such as the outer periphery 12. This provides guidance to a surgeon for the formations of stitches as a continuous circle all about the outer periphery 12. The patch 10 is secured by two substantially concentric circles of stitches, an inner circle being illustrated herein by phantom line 14. A mesh having an outer periphery formed by a radius of approximately 7.5 cm from the center point 15 of the mesh is typically used for the repair of the aforementioned hernias. The inner circle of stitches 14 is preferably spaced about 3.5 cm from the first outer circle of stitches or outer periphery 12.

Figure 5:
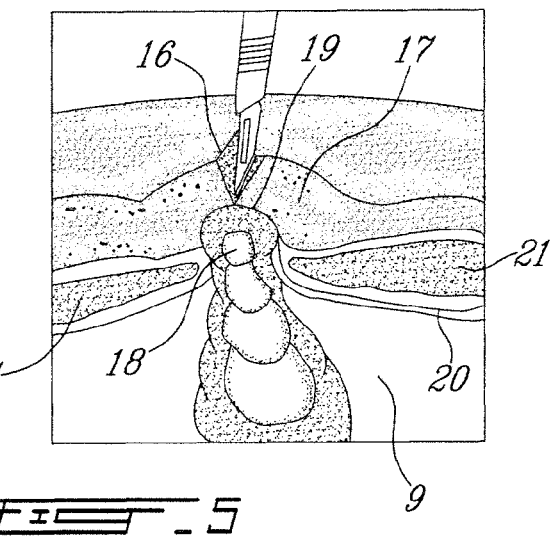
FIG. 5 is a perspective view illustrating an incision or excising a hernia.
Figure 6:
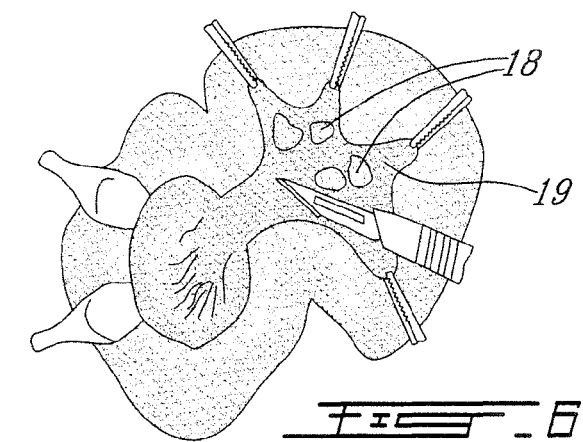
FIG. 6 is a perspective view showing an excision of the hernia sac of a hernia.

FIGS. 5 to 9 briefly illustrate the repair of an abdominal ventral or parastomial hernia wherein, as shown in FIG. 5, an incision 16 is effected in the fatty tissue 17 to expose the hernia 18. The hernia 18 is then excised as shown in FIG. 6 through the wound opening.

Figure 7:
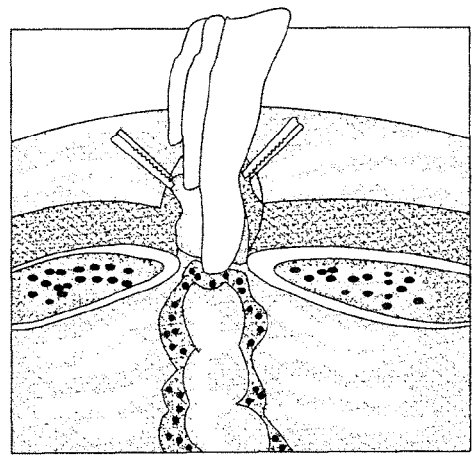
FIG. 7 is a perspective view illustrating how the sac content is reduced after excision.
Figure 9:
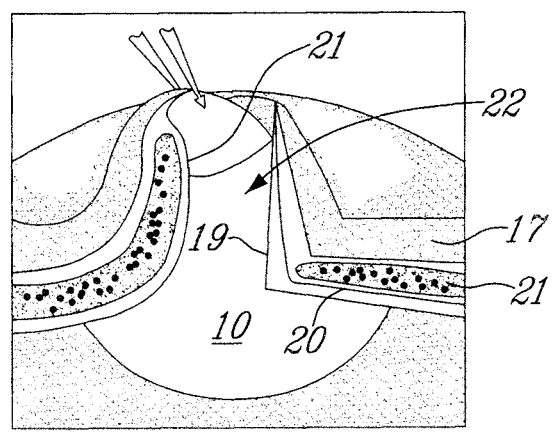
FIG. 9 is a perspective view showing the application of the auto-graft bio-synthetic mesh under the incision for wound closure.
Figure 10:
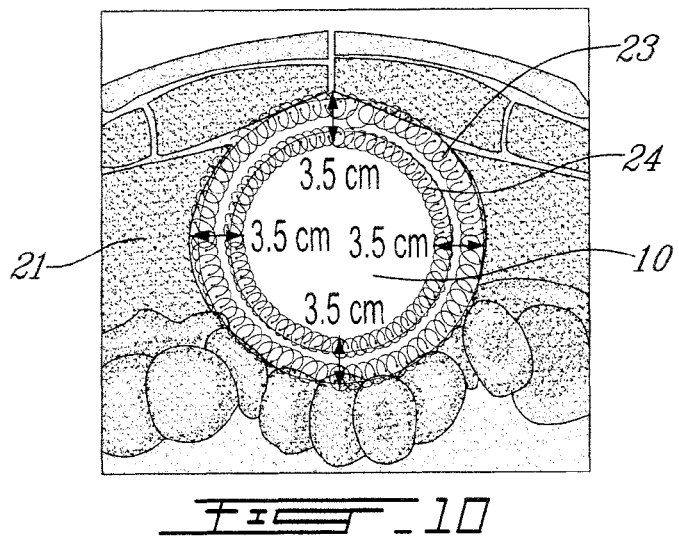
FIG. 10 is a perspective view illustrating the double circular concentric sutures which secure the mesh to the parietal peritoneum and the posterior sheath of the rectus muscle.
Figure 11A:
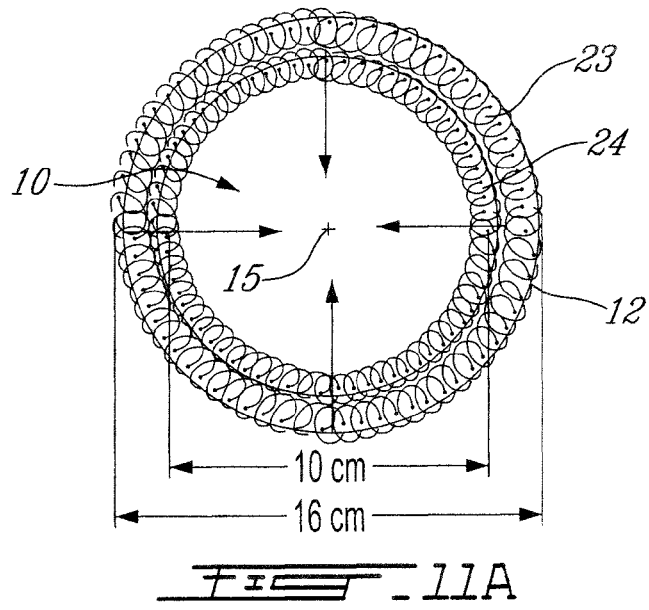
FIG. 11A is a further view showing the dimension of the mesh and the relationship of the double circular concentric sutures.

FIG. 7 illustrates the reduction of the sac contents wherein the mesh 10 of the present invention can now be secured to the parietal peritoneum 19 and the posterior rectus sheath 20 of the rectus muscle 21. As shown in FIG. 9, the bio-synthetic mesh 10 is inserted through the wound opening 22 and the surgeon progressively effects spiral stitches 23, as shown in FIGS. 10 and 11A, all about the outer periphery 12 of the mesh 10 or a delineated circle 12 of the patch 13 to secure the mesh 10 to the parietal peritoneum 19 and the posterior rectus sheath 20. A second row of spiral stitches 24 is then effected at a shorter radius from the center 15 of the patch. Because the mesh is formed of woven polyester or polypropylene fibers they provide elasticity to the patch. The outer circle of spiral stitches 23 applies an external pressure to compress the patch thereby relaxing the central part thereof and effectively reducing the diameter of the patch. The second inner circle of stitches applies an opposite pressure to the outer circle of stitches to substantially remove this relaxed central part of the patch. It is pointed out that both circles of stitches are independent from one another and what follows is an analysis of the membrane deformation and the reason for the two circular rows of stitches.

Figure 11B:
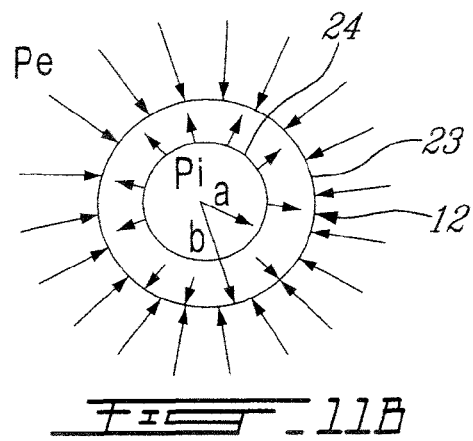
FIG. 11B is a schematic view of the hypothetical model for the two concentric circular sutures.

With reference to FIG. 11B, there is shown a model of the distribution of forces or pressures applied to the mesh by the stitches. While the first outer circle 23 is applying an external pressure p, the second inner circle 24 applies an opposite pressure to remove the central relaxation of the membrane forming the patch. The external circle 23 applies a constant pressure on the outer edge 12 to keep the patch fixed.

Thus, two pressures are applied on the patch, namely an external pressure generated by the external circle and called $p_e$ and internal pressure generated by the internal circle 24 called $p_i$.

By doing these two circles, the two pressures $p_e$ and $p_i$ are applied on the edge of the membrane.

Considering the model illustrated in FIG. 11B, the global hypotheses is analysed as follows:

1. The membrane is considered as an empty disc in the first approximation
   →Pressure (and then forces) are uniformly distributed on the external disc edges
2. The attachment point in this first approximation is not taken into account
3. The membrane is considered as an elastic material with the following constants: E and ν; where E is the Young module and ν the Poisson coefficient.
4. All pressures are supposed to be uniform and constant.

Step 1: Only the first stitches are done to constitute the first external circle ($a=0$ and $p_i=0$).

Hypothesis 1: Assume that the system is a disc with thick edge.

At the steady state the equation that governs the system is as follows:

$$\frac{\partial^2 u}{\partial r^2} + \frac{1}{r}\frac{\partial u}{\partial r} - \frac{u}{r^2} = 0 \quad (1)$$

u being the displacement in the radial direction r.

Then, the solution for equation (1) is as follows:

$$u = C_1 r + \frac{C_2}{r} \quad (2)$$

$C_1$ and $C_2$ are integration constants.

The stress and strain of the system can thus be written as follows:

$$\sigma_r = \frac{E}{1-v^2}\left(\frac{\partial u}{\partial r} + v\frac{u}{r}\right) \text{ (Radial constraint)} \quad (3)$$

$$\sigma_\theta = \frac{E}{1-v^2}\left(\frac{u}{r} + v\frac{\partial u}{\partial r}\right) \text{ (Angular constraint)} \quad (4)$$

Using equation (2), (3) and (4) yields:

$$\sigma_r = \frac{E}{1-v^2}\left(C_1(1+v) - C_2\frac{1-v}{r^2}\right) \quad (5)$$

$$\sigma_\theta = \frac{E}{1-v^2}\left(C_1(1+v) - C_2\frac{1-v}{r^2}\right) \quad (6)$$

Taking into account that the external disc edges are subjected to a non-zero pressure p and the inner edges subjected to zero pressure 0, $C_1$ and $C_2$ expressions can be found from these two boundary conditions, hence:

$$C_1 = \frac{1-v}{E}\frac{-b^2 p}{b^2 - a^2} \quad (7)$$

$$C_2 = \frac{1+v}{E}\frac{a^2 b^2 (-p)}{b^2 - a^2} \quad (8)$$

a and b are, respectively, the outer and inner disc edge.

And so the radial displacement u is defined as follows:

$$u = \frac{1-v}{E}\frac{-b^2 p}{b^2 - a^2}r + \frac{1+v}{E}\frac{a^2 b^2 (-p)}{(b^2 - a^2)r} \quad (9)$$

Step 2: Second stitches are done to constitute the second circle (b'=b−u).

Hypothesis 2: Assume that the system is a disc with thick edge (the stitches thickness is 0.4 mm).

At the steady state the equation that governs the system is as follows:

$$\frac{\partial^2 u'}{\partial r^2} + \frac{1}{r}\frac{\partial u'}{\partial r} - \frac{u'}{r^2} = 0 \quad (10)$$

u being that displacement in the radial direction r. Then, the solution for equation (10) is as follows:

$$u' = C_1 r + \frac{C_2}{r} \quad (11)$$

$C_1$ et $C_2$ are integration constants.

The stress and strain of the system can thus be written as follows:

$$\sigma_r = \frac{E}{1-v^2}\left(\frac{\partial u'}{\partial r} + v\frac{u'}{r}\right) \text{ (Radial constraint)} \quad (12)$$

$$\sigma_\theta = \frac{E}{1-v^2}\left(\frac{u'}{r} + v\frac{\partial u'}{\partial r}\right) \text{ (Angular constraint)} \quad (13)$$

Using equation (11), (12) and (13) yields:

$$\sigma_r = \frac{E}{1-v^2}\left(C_1(1+v) - C_2\frac{1-v}{r^2}\right) \quad (14)$$

$$\sigma_\theta = \frac{E}{1-v^2}\left(C_1(1+v) - C_2\frac{1-v}{r^2}\right) \quad (15)$$

Taking into account that the external disc edges are subjected to a non-zero pressure p and the inner edges subjected to zero pressure 0, $C_1$ and $C_2$ expressions can be found from these two boundary conditions, hence:

$$C_1 = \frac{1-v}{E}\frac{a'^2 p_i - b'^2 p_e}{b'^2 - a'^2} \quad (16)$$

$$C_2 = \frac{1+v}{E}\frac{a'^2 b'^2 (p_i - p_e)}{b'^2 - a'^2} \quad (17)$$

a and b are, respectively, the outer and inner disc edge.

And so the radial displacement u is defined as follows:

$$u' = \frac{1-v}{E}\frac{a'^2 p_i - b'^2 p_e}{b'^2 - a'^2}r + \frac{1+v}{E}\frac{a'^2 b'^2 (p_i - p_e)}{(b'^2 - a'^2)r} \quad (18)$$

Hypothesis 3: The stitches are considered as the thin disc edge. By pulling on the stitches, this will correspond to an external pressure applied on the outer edge of the disc.

Hypothesis 4: Assume that the system is a disc with a thin edge.

Assume that the thickness of the thin edge is $\epsilon$, then $$a' = r - \frac{\varepsilon}{2} \quad (19)$$

$$b' = r + \frac{\varepsilon}{2} \quad (20)$$

r is the mean radius of the disc, which implies:

$$a'^2 = r^2 - r\varepsilon + \frac{\varepsilon^2}{4} = r^2 - r\varepsilon \quad (21)$$

$$b'^2 = r^2 + r\varepsilon + \frac{\varepsilon^2}{4} = r^2 + r\varepsilon \quad (22)$$

Then equation (18) becomes:

$$u' = \frac{1-v}{E}\frac{a'^2 p_i - b'^2 p_e}{b'^2 - a'^2}r + \frac{1+v}{E}\frac{a'^2 b'^2 (p_i - p_e)}{(b'^2 - a'^2)r} \quad (23)$$

$$u' = \frac{1-v}{E}\frac{(r-\varepsilon)p_i - (r+\varepsilon)p_e}{2\varepsilon} + \frac{1+v}{E}\frac{(r^2 - \varepsilon^2)(p_i - p_e)}{2\varepsilon}$$

Equation (23) corresponds to the global deformation of the patch taking into account all of the assumptions.

Reference is made to the following publication: Résistance des matériaux, A. Bazergui et al., 3$^{ème}$ édition, Presses Internationales Polytechnique.

It is pointed out that the fibers of the patch may also be coated with the patient's own tissue or collagen at a suitable time prior to performing the surgical intervention. Still further the mesh may be formed of bio-degradable polymers and these may be coated with patient tissue culture prior to the intervention with the fibers acting as a scaffold for the culture. After a predetermined time period, after implantation in a patient, such biodegradable polymers will completely be absorbed and disappear and the patient's own tissue would remain for the hernia repair. The collagen is developed from dermal tissue of the patient and processed with agents to remove cellular elements prior to surgery whereby the patch is bio-compatible and non-carcinogenic. By growing such tissue culture many complications relating to synthetic material implantations can be avoided. Because the fibers provide a scaffold for tissue culture, a patch can be fabricated which is less susceptible to shrinkage/contraction complications after securement in a patient. The tissue culture also isolates the fibers from the patient's structure.

It is pointed out that the new technique in open intra-abdominal ventral herniorrhaphy described herein does not necessitate raising/dissecting large subcutaneous flaps and without bilateral fascial relaxing incisions. The technique is very fast and provides a painless wound closure in the post operative period. The patch and its securement technique can be used in all kinds of ventral or parastomal hernia repair, especially in obese patients for abdominal wall reconstruction. It is an open, tension free ventral hernia repair. It could be used also in laparoscopic repair of ventral and parastomal hernia with a special intra-abdominal device for automatic suturing of the mesh.

It is pointed out that the old incision is not excised at the beginning of surgery. Since these hernias are multilocular, there may be multiple defects separated by fibrous septa and caution is exercised to avoid entering the bowel.

Also, with the repair procedure of the present invention, dissection is not extended beneath the subcutaneous fat in all directions until normal aponeurotic structure is visualized surrounding the defect. The parietal peritoneum is entered and the sac contents reduced, as shown in FIGS. 5 and 6. The large hernia sac is excised. All intra-abdominal adhesions are lysed without compromising the bowel structure. As described above, if the polyester or polypropylene mesh is protected with the patient's tissue, this could potentially avoid seroma formation. The flexibility of the mesh is also essential for the approximation of the rectus abdominis muscles. The mesh is also tailored depending upon the size of the hernia.

The first row of polypropylene spiral suture is passed from the extreme edge 12 of the circular mesh or the outer delineation of a patch by taking the full thickness of the wall including the parietal peritoneum and the posterior rectus sheath. The first outer circle of sutures is used only for anchoring the mesh and for reducing the aperture of the incision. The second inner circle of sutures creates a tension on the abdominal wall intraperitoneally causing an approximation of the rectus abdominis muscles to its normal position as well as both edges of the wound creating an overlapping condition. This new anatomical condition will necessitate an excision of both edges of the skin and subcutaneous tissue for cosmetic wound closure. A third circular row of sutures could be done if necessary depending on the size of the mesh.

Reconstruction of the abdominal wall can be done with this new intraperitoneal approach. There is also no need for approximation of the fascia. Special polymeric medicated suture clips 30 or 50, as shown in FIGS. 12-17, encapsulated with an analgesic (Xylocaine) for controlled release of the analgesic for 7-10 days would provide a pain-free recovery period and a closed wound suction drain is placed in the subcutaneous space.

Prophylactic pre-operative antibiotics may be administered during the induction of the general anesthesia and this is optional. Antibiotics will be stopped after the retrieval of the suction. There is also no need for abdominal binder or other compressive garment.

To avoid potential complications of synthetic meshes currently available in the market, the auto-graft mesh 10 could also use translational tissue engineering technology to improve human tissue culture. Characteristics of an ideal mesh for abdominal wall reconstruction would have the following characteristics:
a) Biocompatibility and noncarcinogenecity.
b) Ability to withstand physiologic stresses over a long period.
c) Promotes strong tissue in-growth.
d) Without substantial contraction/shrinkage.
e) Without development of adhesions to visceral structures and fistula formation.
f) Resistance to bacterial colonization and infection.
g) Without pain after implantation.
h) Without formation of an enterocutaneous fistula.
i) Without recurrence.
j) Without seroma formation.

The ideal mesh, respecting all the above characteristics, is possible by developing a composite mesh with synthetic and biologic components. The biologic component could be provided from the patient before surgery. The donor source is the patient himself (e.g. extensive 3$^{rd}$ degree burn patients). Dermal tissue (auto-graft) processed with various agents to remove cellular elements and develop large sheets of collagen which are incorporated on the synthetic mesh (polyester or polypropylene) in a specialized laboratory before surgery. The idea is to develop exactly the same phenomenon which happens in humans after implantation a synthetic mesh. As mentioned above, the synthetic mesh (polyester, polypropylene) can be used as a scaffold for tissue culture. Protection of a synthetic mesh with patient collagen (auto-graft) could avoid the complications encountered with unprotected mesh placed in an intra peritoneal position in direct contact with the viscera such as: fistula formation, adhesions, erosion, inflammatory reaction, reduce infection recurrence rate due to the description of the new technique without bilateral fascial incision without raising/dissecting extensive subcutaneous flaps.

Advantages of the auto-graft bio-synthetic mesh 10 of the present invention are as follows:
1) Obviously, it is biocompatible and non carcinogenic.
2) Since it can be an almost normal human membrane it could withstand physiologic stresses.

3) Since it is vascularized before its implantation thereby will have the ability to promote tissue in-growth and clear growth/infection.
4) Since it is an auto-graft will not induce adhesions to visceral structures and avoid fistula formation.
5) Experimental data shows that using macroporous polyester (PE) and polypropylene (PP) in hernia repair the measured shrinkage were respectively 13% for (PE) and 5% for PP and 57% for ePTFE. Using PE and PP as a scaffold for tissue culture it is assumed that the tendency for shrinkage could most probably be reduced in importance. The usage of the new auto-graft mesh could bring a beneficial impact on shrinkage/contraction complication. It is also assumed that the recurrence rate could be reduced if we take into consideration the co-morbid conditions of the patient, hernia size, wound infection, improper mesh fixation.
6) It is also assumed that the pain could be reduced significantly because there is no synthetic material in contact with visceral and the subcutaneous structures.
7) Since there is no direct contact of the synthetic material with the patient structures there will be no host inflammatory reaction to the implanted material and consequently no seroma. Haematoma contribution to the formation of the seroma is dealt with by closed drainage of the wound.

Figure 12:
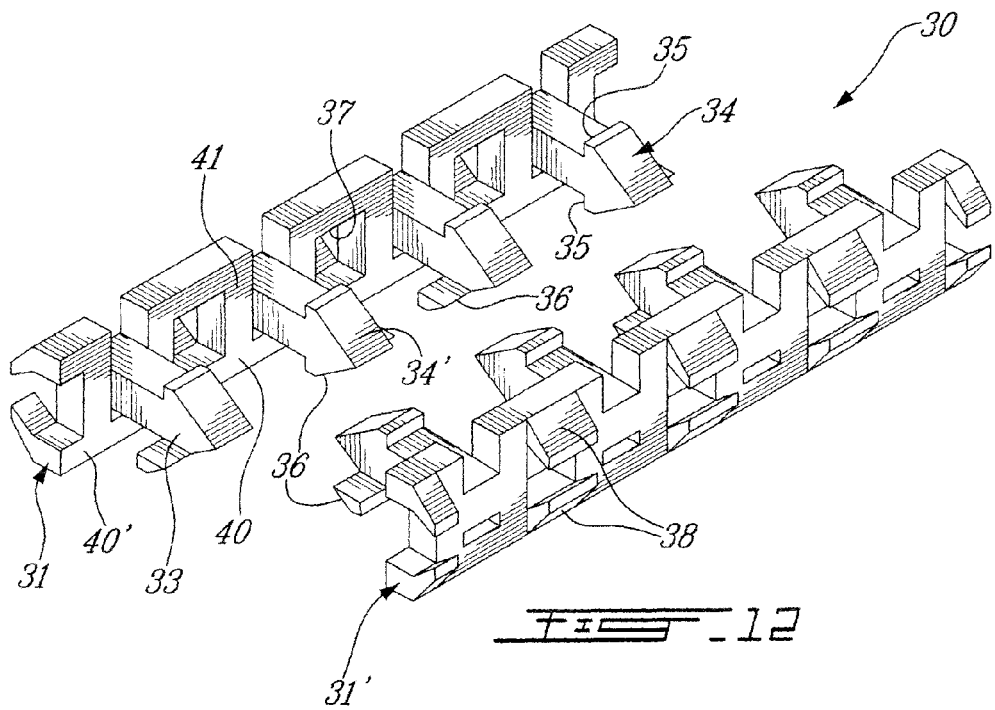
FIG. 12 is a perspective view of a first embodiment of a suture clip constructed in accordance with the present invention and wherein the pair of identical flexible compression strips are shown in a non-engage position.
Figure 13:
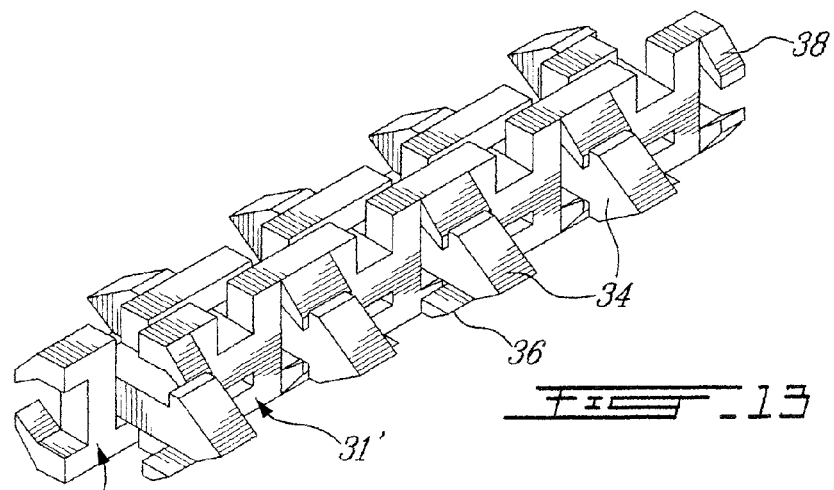
FIG. 13 is a perspective view similar to FIG. 12 but showing the pair of identical flexible compression strips in engagement.
Figure 14:
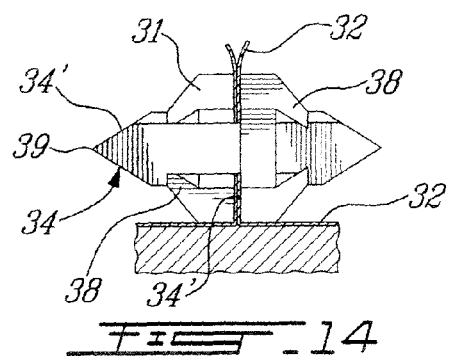
FIG. 14 is a transverse section view of FIG. 13 showing the relationship between both compression strips when engaged to clamp bodily soft tissue.

Referring now to FIGS. 12 to 14, there will be described a first embodiment of a suture clip for joining portions of bodily soft tissue. The suture clip 30, as shown in FIG. 12, is comprised of a pair of identical flexible compression strips, herein strips 31 and 31' which are configured and adapted to interlock with one another with portions of bodily soft tissue 32 compressed therebetween, as shown in FIG. 14. The compression of the bodily soft tissue 32 arrests the blood vessels therein. Each of the compression strips 31 and 31' have at least two equidistantly spaced-apart tissue piercing teeth 33, herein only four illustrated but a plurality of these can be located along a compression strip. The tissue piercing teeth 33 project from a clamping surface 40' of the bottom support base 40.

Each tissue piercing tooth 33 has a pointed free end portion 34 having a piercing tip end 39. Latch formations 35 are formed behind the pointed free end portion 34. The tissue piercing teeth 33 have a tapered face extension 36 below the teeth and this is designed to compress the cut edge of the tissue preventing the flow of blood. The tapered face extension 36 allows the tissue to gradually open up ensuring that an optimal compression zone is achieved for healing.

The compression strips 31 and 31' are also provided with retention means which are comprised by a tooth latching guide openings 37 formed above the clamping surface and extending between each of the tissue piercing teeth 33. Flexible arresting means in the form of flexible lips 38 are formed integral with the compression strip and disposed on opposed sides of the tooth latching guide opening 37 and aligned for frictional contact with the opposed outwardly sloped walls 34' and 36 of the pointed free end portion 34 of the tissue piercing teeth 33 and biased for captive engagement thereof with the abrupt rear edges or latch formations 35 of the pointed free end portion 34. It is pointed out that the entire component parts of the compression strips are integrally molded.

As can be seen in FIG. 14, the piercing teeth 33 extend forwardly of the clamping surface 34 in a transverse direction. Each of the pointed free end portions has opposed outwardly sloped walls 34' extending rearwardly from a piercing tip 39 of the tissue piercing teeth 33.

The flexible compression strips 31 and 31' are constructed of a bio-degradable polymer and a substance such as an anesthetic, an analgesic and an antibiotic substance is integrated in at least one of the flexible compression strips for providing comfort to the patient after the closure of the incision. As hereinshown, the compression strips 31 and 31' are straight strips. The tooth latching guide opening 37 is formed in a rectangular wall formation 41 extending above the bottom support base 40 between adjacent ones of the tissue piercing teeth 33. The tooth latching guide opening 37 is hereinshown as having a square guide opening 37 for receiving the pointed free end portion of the piercing teeth therethrough. The teeth are also of square cross-section.

FIGS. 13 and 14 illustrate the compression strips 31 and 31' engaged with one another in an offset relationship with the latch formations 35 engaged with the flexible lips 38 and thus preventing separation of the strips when engaged with one another. A suitable applicator device, not shown herein, is provided for positioning the compression strips and applying them to compress the soft bodily tissues 32 therebetween, as illustrated in FIG. 14.

Figure 15:
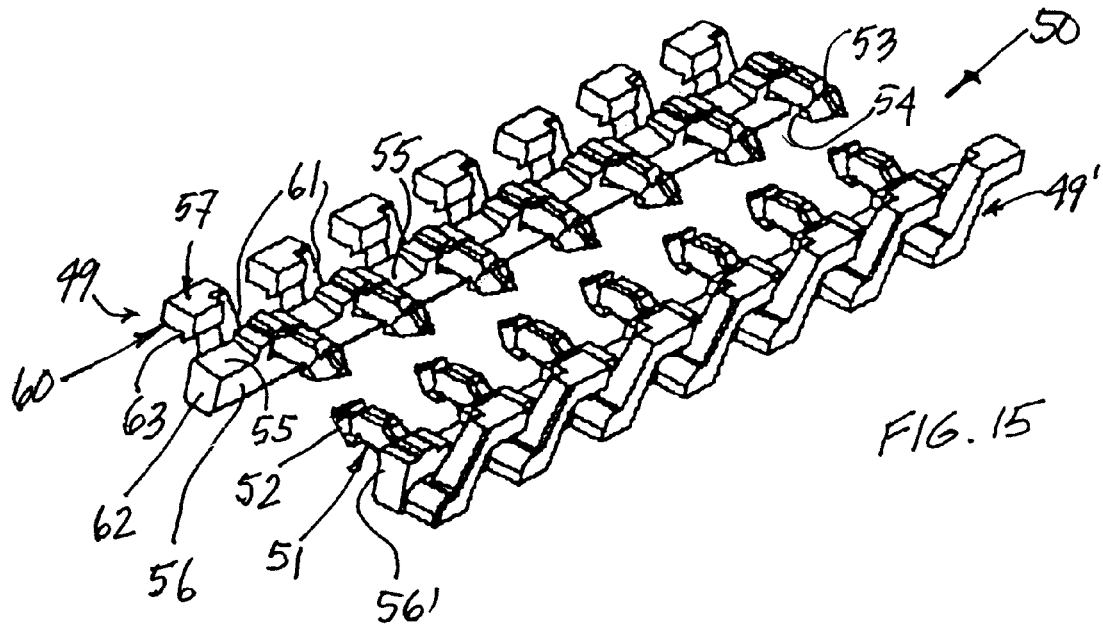
FIG. 15 is a perspective view of a further embodiment of a suture clip constructed in accordance with the present invention and wherein the pair of identical flexible compression strips are shown in a non-engaged position.
Figure 16:
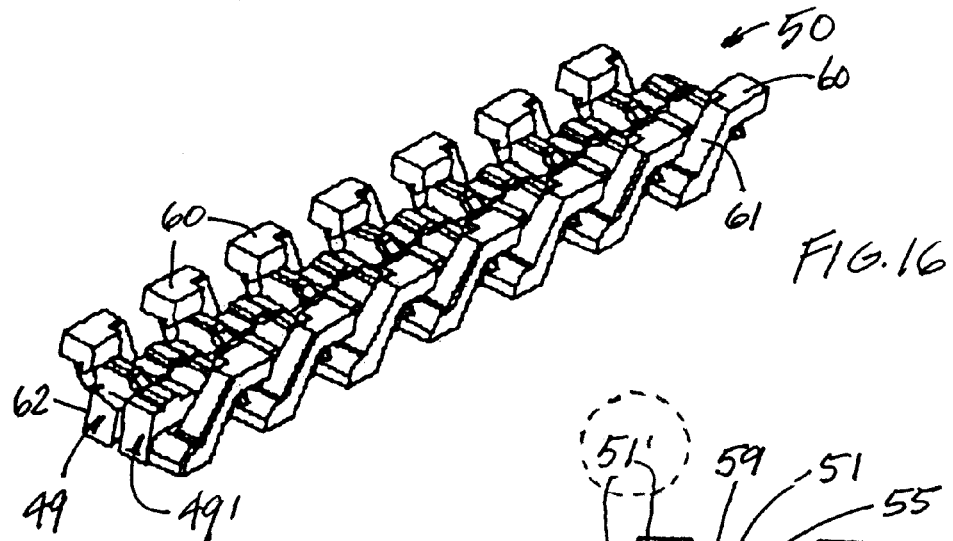
FIG. 16 is a perspective view showing the compression strips of FIG. 15 in an engaged position.
Figure 17:
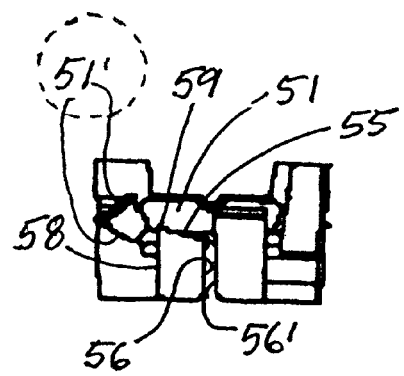
FIG. 17 is a transverse section view of the compression strips of FIG. 16 showing the relationship therebetween when in an engaged condition.

Referring now to FIGS. 15 to 17, there is shown another embodiment of a suture clip 50 constructed in accordance with the present invention. The clamping surface 56 is formed in the base 62 as with the embodiment illustrated in FIG. 12. As hereinshown the tissue piercing teeth 51 are similar to the teeth 33, as shown in FIG. 12, and the pointed free end portion 52 thereof are each provided with outwardly sloped flat walls 51' and latch formations, herein vertically offset engaging notches 53 and 54. The retention means is herein comprised by tooth latching guide ramps 55 disposed between each of the tissue piercing teeth 51 and extending rearwardly from the clamping surface 56. Each of the tooth latching guide ramps 55 has a fixed arresting means in the form of an abrupt rear edge 58 which defines in an uppermost part thereof, at the junction with the flat upwardly sloped top face of the guide ramp 55, a rear pointed edge 59 adapted to engage in the notch 54 of the tissue piercing tooth 51, as shown in FIG. 17. A flexible arresting means 57 has a gripping head 60 integrally formed and supported in spaced alignment above the tooth latching guide ramp by a flexible post 61 interconnecting the gripping head 60 with the base 62 of the flexible compression strips 49 and 49'. A gripping edge formation 63 is integrally formed in the gripping head 60 and adapted to engage with the notch 53 behind the pointed free end portion 52 of the tissue piercing teeth 51.

As shown in FIGS. 16 and 17, when the compression strips 49 and 49' are brought together in offset mating relationship, the pointed free end portion 52 of the tissue piercing teeth 51 guide the teeth on the tooth latching guide ramp 55 whereby the notches 53 and 54 become locked between the pointed edge 59 formed in the rear edge of the top face of the ramp and the gripping edge formation 63 formed in the flexible gripping head 60. Thus, soft tissue is clamped between the opposed clamping surfaces 56 and 56' of the compression strips. It is also pointed out that with both embodiments of the suture clip, as the compression strips are brought closer together with bodily soft tissue positioned therebetween, the tissue piercing teeth pierce through the soft tissue to clamp the soft tissue therebetween as illustrated at 32 in FIG. 14.

It is within the ambit of the present invention to cover any obvious modifications of the preferred embodiment described herein, provided such modifications fall within the scope of the appended claims.

I claim:
1. A suture clip for joining portions of bodily soft tissue, said suture clip comprising a pair of identical flexible com- pression strips formed of a biodegradable and bio-absorbable polymer and adapted to interlock with one another with said portions of said bodily soft tissue compressed therebetween to arrest blood vessels in said portions of said bodily soft tissue, each said compression strip having at least two equidistantly spaced-apart tissue piercing teeth projecting forwardly of a flat clamping surface of said strip, each said piercing tooth having a pointed free end portion and opposed latch formations, each said latch formation being disposed to a respective one of opposed top and bottom sides of said piercing teeth for latching engagement of said latch formations, said compression strips having spaced-apart tooth latching guide ramps extending rearwardly from said clamping surface and disposed on opposed sides of said tissue piercing teeth, said tooth latching guide ramps being angulated rearwards and having a fixed arresting means formed in a rear edge thereof, each said pointed free end portion of said piercing tooth having opposed outwardly sloped flat walls extending rearwardly from said pointed free end portion of said tooth, said opposed outwardly sloped flat walls terminating in an abrupt rear edge of said piercing tooth to constitute said latch formations, and each compression strip having a flexible arresting means projecting above each said latching guide ramp and the flexible arresting means has a gripping edge formation facing said latching guide ramp, said compression strips when brought together in offset mating relationship causing said piercing teeth to be displaced on said tooth latching guide ramps until said latch formations of said piercing teeth become locked between said fixed arresting means of said guide ramps and said gripping edge formations of said flexible arresting means.

2. A suture clip as claimed in claim 1 wherein at least one of an anesthetic, an analgesic and an antibiotic substance is integrated in at least one of the flexible compression strips.

3. A suture clip as claimed in claim 1 wherein said fixed and flexible arresting means are vertically aligned engaging notches adapted to be engaged by associated ones of said opposed latch formations of said piercing tooth.

4. A suture clip as claimed in claim 3 wherein said fixed arresting means of said tooth latching guide ramp is constituted by a rear pointed edge formed between a flat upwardly sloped top face of said guide ramp and said rear edge thereof.

5. A suture clip as claimed in claim 4 wherein said gripping edge formation of said flexible arresting means is constituted by a gripping edge formation formed in a gripping head of said flexible arresting means, said gripping head being supported in spaced alignment above said tooth latching guide ramp and a flexible post interconnecting said gripping head with a base of said flexible compression strip, said base defining said clamping surface.

* * * * *